(12) United States Patent
Kazumori

(10) Patent No.: US 6,600,156 B2
(45) Date of Patent: Jul. 29, 2003

(54) SCANNING ELECTRON MICROSCOPE

(75) Inventor: Hiroyoshi Kazumori, Tokyo (JP)

(73) Assignee: JEOL Ltd., Tokyo (JP)

( * ) Notice: Subject to any disclaimer, the term of this patent is extended or adjusted under 35 U.S.C. 154(b) by 98 days.

(21) Appl. No.: 09/917,285

(22) Filed: Jul. 27, 2001

(65) Prior Publication Data
US 2002/0024014 A1 Feb. 28, 2002

(30) Foreign Application Priority Data

Jul. 28, 2000 (JP) ........................................ 2000-228717

(51) Int. Cl.[7] ................................................. H01J 37/14
(52) U.S. Cl. ................................ 250/310; 250/396 ML
(58) Field of Search ............................. 250/310, 396 R, 250/396 ML, 396 MC

(56) References Cited

U.S. PATENT DOCUMENTS

| | | | |
|---|---|---|---|
| 5,010,253 A | * 4/1991 | Braglia et al. | .............. 250/399 |
| 5,412,210 A | 5/1995 | Todokoro et al. | ........... 250/310 |
| 6,295,333 B1 | * 9/2001 | Tamura | ....................... 378/44 |
| 6,320,194 B1 | * 11/2001 | Khursheed et al. | .... 250/442.11 |
| 6,407,387 B1 | * 6/2002 | Frosien et al. | .............. 250/310 |

* cited by examiner

Primary Examiner—John R. Lee
Assistant Examiner—Phillip A Johnston
(74) Attorney, Agent, or Firm—Webb Ziesenheim Logsdon Orkin & Hanson, P.C.

(57) ABSTRACT

A scanning electron microscope comprises: an electron gun for emitting an electron beam; a system of condenser lenses; scanning coils; and an objective lens having inner and outer magnetic polepieces to form a magnetic field lens below the lower ends of the polepieces. The inner and outer polepieces are provided with mutually communicating bores via which the backscattered electron detector can be withdrawably inserted into the electron beam path within the objective lens.

10 Claims, 5 Drawing Sheets

PRIOR ART

PRIOR ART

PRIOR ART

SCANNING ELECTRON MICROSCOPE

BACKGROUND OF THE INVENTION

1. Field of the Invention

The present invention relates to a scanning electron microscope equipped with an objective lens that incorporates a detector.

2. Description of the Related Art

In a scanning electron microscope, as an electron beam hits a specimen, secondary electrons, backscattered electrons, X-rays, and cathodoluminescence are produced, and these are detected. In a scanning electron microscope, the shape of the objective lens is an important factor that determines the instrumental resolution. Today, an objective lens for developing a magnetic field lens below the lower ends of inner and outer polepieces (i.e., toward the specimen) is widely used as an objective lens for achieving high resolution.

FIG. 2 shows the main portion of a scanning electron microscope equipped with this type of objective lens. In this figure, the objective lens is indicated by numeral 1 and consists of an inner polepiece 2, an outer polepiece 3, a yoke 7, and a coil 8. The objective lens is so designed that the magnetic field reaches a specimen 4.

Bores H1 and H2 are formed in the inner polepiece 2 and outer polepiece 3, respectively, of the objective lens 1. A secondary electron detector 5 is mounted in these holes. A positive voltage is applied to the front end of the secondary electron detector 5 to attract secondary electrons.

Secondary electrons se produced by illumination of the electron beam on the specimen 4 are directed upward through the objective lens 1 by the magnetic field produced by the objective lens 1. The secondary electrons se are accelerated by the action of an electric field formed ahead of the front end of the secondary electron detector 5, and are detected by the secondary electron detector 5.

Electron beam impingement on the specimen 4 also produces backscattered electrons be, which are detected by a backscattered electron detector 6 mounted below the polepieces of the objective lens 1, the detector 6 consisting of a semiconductor device. Usually, this backscattered electron detector 6 assumes a doughnut-like form and is centrally provided with an electron beam passage bore H0.

Where the specimen is subjected to an elemental analysis or other analysis, an X-ray analytical instrument is interfaced with the scanning electron microscope, and X-rays produced as a result of electron beam impingement on the specimen are detected. In this case, the X-ray detector of the X-ray analytical instrument is mounted on the sidewall of the specimen chamber between the objective lens 1 and the specimen 4 such that the X-ray detecting surface faces toward the optical axis O. Furthermore, the specimen is tilted such that the specimen surface faces the X-ray detector, in order that X-rays emanating from the specimen are efficiently detected by the X-ray detector.

The above-described objective lens 1 has the built-in secondary electron detector 5. Therefore, in a scanning electron microscope equipped with such an objective lens, the secondary electron detector is not installed between the objective lens 1 and the specimen 4. Consequently, the distance, or the working distance (WD), between the objective lens 1 and the specimen 4 can be set small. Hence, the aberration coefficient of the objective lens 1 can be made small. As a result, a high-resolution secondary electron image can be obtained.

On the other hand, backscattered electrons have much higher energies than secondary electrons and, therefore, backscattered electrons traveling at angles greater than a given angle with respect to the optical axis O bounce off the objective lens field as shown in FIG. 3(a) and thus travel at greater angles. These backscattered electrons are indicated by be2. Those of the backscattered electrons which are traveling within the given angle are restricted by the objective lens field and pulled upward beyond the center of the objective lens 1 along the optical axis O. These backscattered electrons are indicated by be1.

Accordingly, backscattered electrons incident on the backscattered electron detector 6 are small in quantity. In consequence, the backscattered electron image is a coarse image of insufficient brightness.

Therefore, if the specimen 4 is moved downward (i.e., the working distance is increased) as shown in FIG. 3(b), the effect of the objective lens field on the electrons backscattered out of the specimen 4 weakens. Therefore, most of the electrons be backscattered out of the specimen 4 and traveling at angles less than a given angle with respect to the optical axis O impinge on the backscattered electron detector 6. The result is that a backscattered electron image of high brightness can be obtained.

However, where secondary electron images and backscattered electron images should be alternately obtained under optimum conditions from the same field of view to make a structural analysis of the sample or for other purpose, if a secondary electron image is obtained, it is necessary to set the working distance shorter to establish high-resolution conditions. If a backscattered electron image is obtained, it is necessary to set the working distance greater to enhance the detection efficiency and establish high-brightness conditions. That is, the working distance needs to be increased and reduced alternately by adjusting the height of the specimen stage (not shown) taken along the Z-axis. Consequently, the operability is poor. Furthermore, the magnification is varied when the working distance is varied. Therefore, the magnification needs to be corrected when either image is obtained.

In addition, the thickness of the backscattered electron detector 6 is normally about 3 to 5 mm. Since this detector is mounted to the undersides of the polepieces of the objective lens 1 as shown in FIG. 2, the working distance (WD) cannot be decreased.

Moreover, where X-rays from the specimen are detected by an X-ray detector, the specimen must be tilted. This makes it impossible to reduce the working distance. For this reason, the objective lens used as a high-resolution objective lens cannot exhibit its performance fully.

SUMMARY OF THE INVENTION

It is an object of the present invention to provide a scanning electron microscope capable of obtaining a high-resolution secondary electron image and a high-brightness backscattered electron image from the same field of view and of performing high-sensitivity X-ray analysis.

The present invention provides a scanning electron microscope comprising: an electron gun for emitting an electron beam; a system of condenser lenses for focusing the electron beam emitted from the electron gun; a scanning means for scanning a specimen with the electron beam emitted from the electron gun; an objective lens having inner and outer magnetic polepieces to form a magnetic field lens below the lower ends of the polepieces; and a backscattered electron detector for detecting electrons backscattered out of the specimen. The inner and outer magnetic polepieces are provided with bores via which the backscattered electron detector can be withdrawably inserted into the electron beam path within the objective lens.

The present invention also provides a scanning electron microscope comprising: an electron gun for emitting an electron beam; a system of condenser lenses for focusing the electron beam emitted from the electron gun; a scanning means for scanning a specimen with the electron beam emitted from the electron gun; an objective lens having inner and outer magnetic polepieces to form a magnetic field lens below the lower ends of the polepieces; and an X-ray detector for detecting X-rays emitted from the specimen. The inner and outer magnetic polepieces are provided with bores via which the X-ray detector can be withdrawably inserted into the electron beam path within the objective lens.

In addition, the present invention provides a scanning electron microscope comprising: an electron gun for emitting an electron beam; a system of condenser lenses for focusing the electron beam emitted from the electron gun; a scanning means for scanning a specimen with the electron beam emitted from the electron gun; an objective lens having inner and outer magnetic polepieces to form a magnetic field lens below the lower ends of the polepieces; and a cathodoluminescence detector for detecting cathodoluminescent light emitted from the specimen. The inner and outer magnetic polepieces are provided with bores via which the cathodoluminescence detector can be withdrawably inserted into the electron beam path within the objective lens.

Further, the present invention provides a scanning electron microscope comprising: an electron gun for emitting an electron beam; a system of condenser lenses for focusing the electron beam emitted from the electron gun; a scanning means for scanning a specimen with the electron beam emitted from the electron gun; and an objective lens having inner and outer magnetic polepieces to form a magnetic field lens below the lower ends of the magnetic polepieces. The inner and outer polepieces of the objective lens are provided with bores, three in total, via which a backscattered electron detector, an X-ray detector, and a cathodoluminescence detector can be withdrawably inserted into the electron beam path within the objective lens.

Other objects and features of the invention will appear in the course of the description thereof, which follows.

DESCRIPTION OF THE PREFERRED EMBODIMENTS

Figure 1:
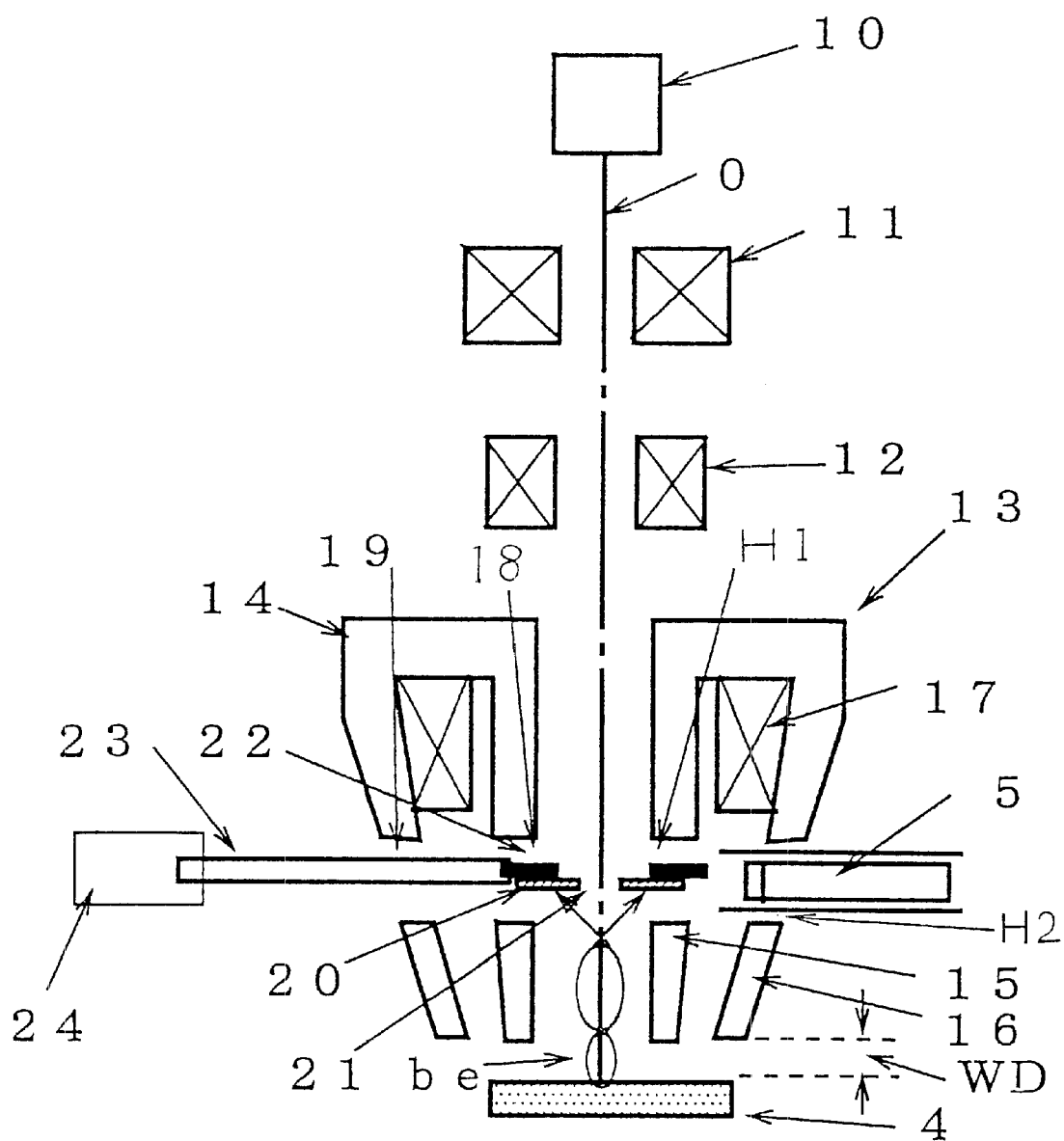
FIGS. 1(a) and 1(b) are schematic views of scanning electron microscopes in accordance with the present invention.
Figure 1:
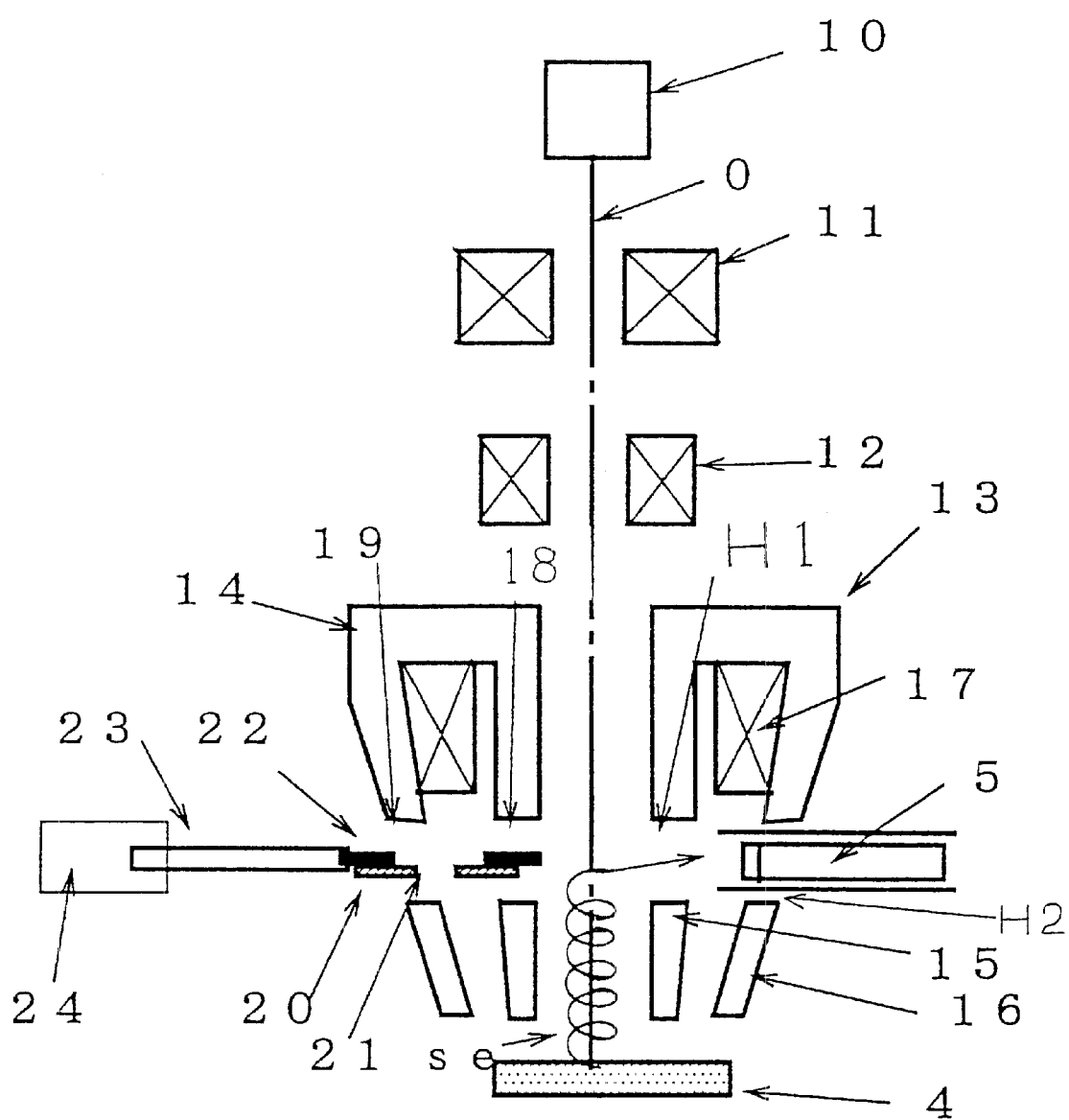
Figure 2:
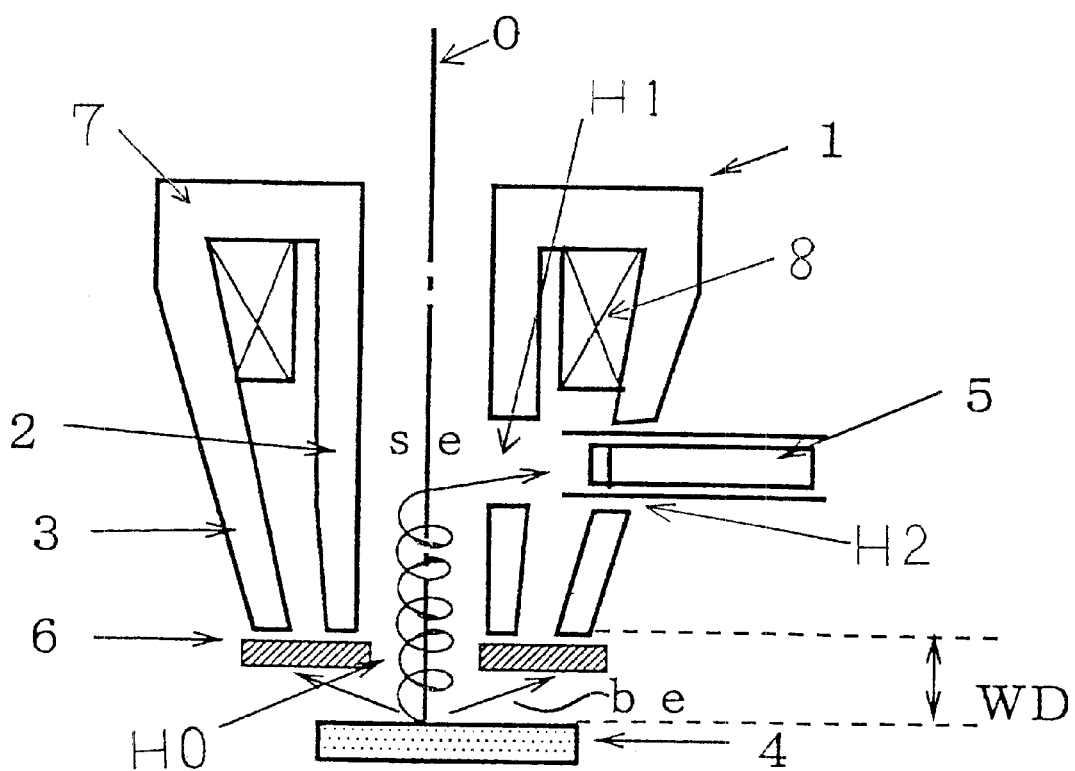
FIG. 2 is a schematic view of an objective lens used in the prior art scanning electron microscope.
Figure 3:
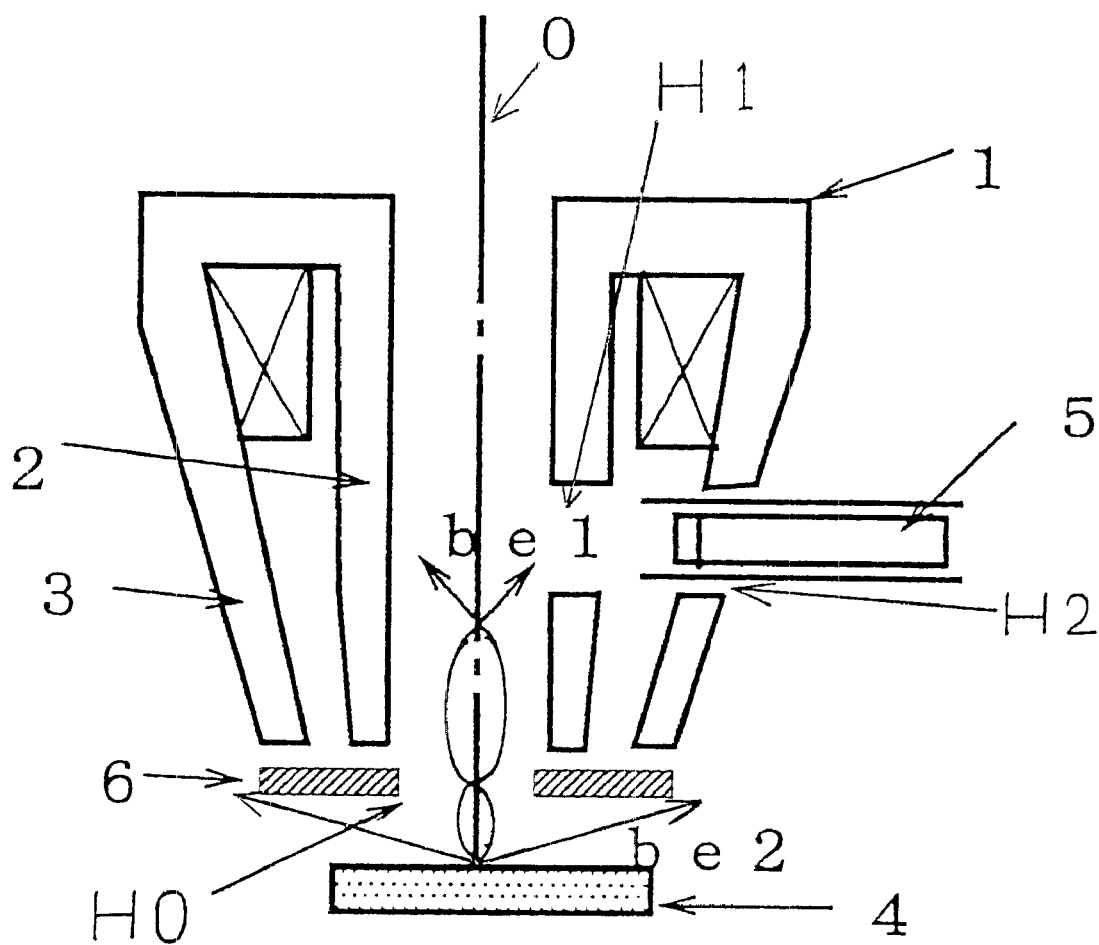
FIGS. 3(a) and 3(b) show the manner in which backscattered electrons are detected in the prior art scanning electron microscope.
Figure 3:
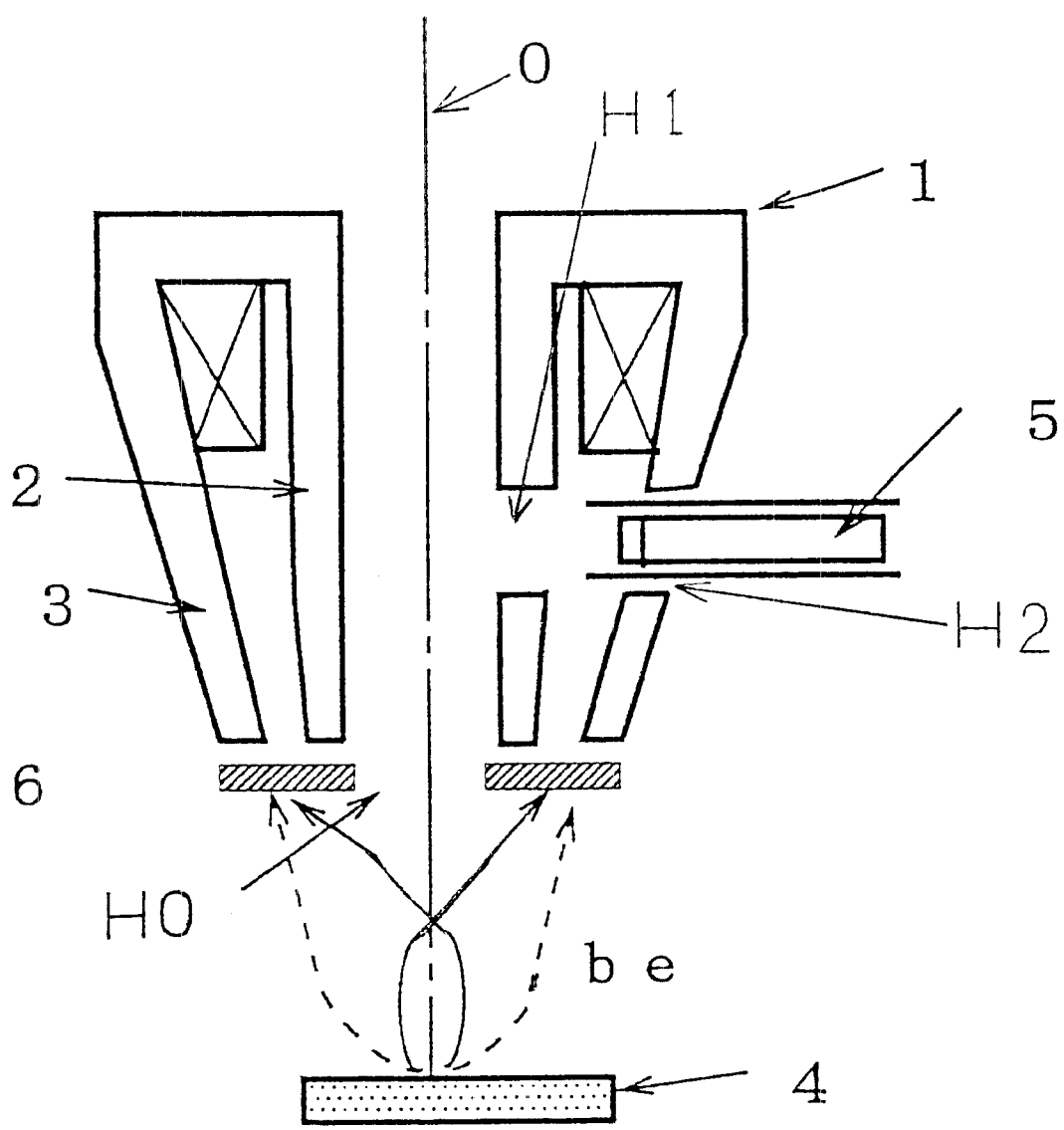

A scanning electron microscope in accordance with the present invention is shown in FIGS. 1(a) and 1(b). Note that like components are indicated by like reference numerals in FIGS. 1(a), 1(b), and 2.

Referring to FIGS. 1(a) and 1(b), an electron gun 10 produces a primary electron beam that is sharply focused onto a specimen 4 by a system of condenser lenses 11 and an objective lens 13. The primary electron beam is scanned in two dimensions across the specimen 4 by the deflection action of scanning coils 12 mounted above the objective lens 13.

The objective lens 13 is made up of a yoke 14, an inner magnetic polepiece 15, an outer magnetic polepiece 16, and a coil 17. The inner polepiece 15 is provided with a bore H1. In addition, the inner polepiece 15 is provided with a bore 18 in its portion opposite to the bore H1. The portion of the outer polepiece 16 that is opposite to the bore 18 is provided with a bore 19.

A backscattered electron detector 20 is shaped in a doughnut-like form and centrally provided with an electron beam passage bore 21 having a diameter of about 2 mm. This detector 20 is mounted on a thin doughnut-like plate 22 that is slightly larger than the detector 20. This plate 22 is supported by a support member 23.

This support member 23 is driven by a drive mechanism 24 mounted outside the scanning microscope column. The plate 22 and backscattered electron detector 20 integrated with the support member 23 can be moved back and forth in the bores 18 and 19 within the objective lens 13 by operating the drive mechanism 24.

FIG. 1(a) shows the manner in which the backscattered electron detector 20 is placed on the optical axis O by such an operation. FIG. 1(b) shows the manner in which the detector 20 has been placed away from the optical axis O.

Where a secondary electron image is observed with this instrument, the drive mechanism 24 is so operated that the backscattered electron detector 20 and the plate 22 that are coupled together are placed sufficiently remotely from the optical axis O as shown in FIG. 1(b), i.e., such that they affect neither the primary electron beam nor the secondary electrons. Conditions for achieving high-resolution images are established. That is, the specimen 4 is moved, and the working distance (WD) is set to approximately 3 mm. This reduces the aberration coefficient of the objective lens 13.

Under these conditions, the primary electron beam is made to scan the specimen 4 in two dimensions by the deflection action of the scanning coils 12. As a result of this scan, secondary electrons se emitted from the specimen 4 are affected by the magnetic field of the objective lens 13 and move upward along the optical axis O through the objective lens 13. Because a positive voltage is applied to the front end of the secondary electron detector 5, the electric field reaches the vicinities of the bore H1 in the inner polepiece 15. Because of this electric field, the secondary electrons are deflected toward the secondary electron detector 5 and detected by it. Since the output signal from this detector 5 representative of the detected secondary electrons is supplied to a display unit via an amplifier and other components (not shown), a secondary electron image of the specimen is displayed on the display unit.

When a backscattered electron image should be observed, the drive mechanism 24 is operated in such a manner that the center of the electron beam passage bore 21 in the backscattered electron detector 20 is brought substantially onto the optical axis O as shown in FIG. 1(a).

Backscattered electrons be emitted from the specimen 4 at angles less than a given angle with respect to the optical axis O as a result of the scan of the primary electrons across the specimen are pulled upward by the magnetic field of the objective lens 13 and move upward along the optical axis O through the objective lens 13. The electrons be are detected by the backscattered electron detector 20.

Because the backscattered electron detector 20 is placed close to and around the optical axis O within the objective lens 13 in this way, the electrons be backscattered out of the specimen can be efficiently detected by the backscattered electron detector 20. Therefore, a high-brightness backscattered electron image can be observed at the same position where a high-resolution secondary electron image is observed without the need for increasing the working distance (i.e., at the same working distance).

Where an elemental analysis or other analysis of the specimen is performed, the backscattered electron detector 20 shown in FIGS. 1(a) and 1(b) is replaced by an X-ray detector. This X-ray detector is shaped in a doughnut-like form centrally provided with an electron beam passage bore. This detector is mounted on the plate 22. X-rays emitted by illumination of the electron beam on the specimen 4 travel upward along the optical axis O through the objective lens 13 and are detected by the X-ray detector. Since the X-ray detector is placed close to and around the optical axis O inside the objective lens 13 in this way, X-rays emitted from the specimen can be detected efficiently by the X-ray detector. Therefore, an X-ray analysis can be performed at high sensitivity at the same position where a high-resolution secondary electron image is obtained without the need to tilt the specimen 4 (i.e., at the same working distance).

If the backscattered electron detector shown in FIGS. 1(a) and 1(b) is replaced by a cathodoluminescence detector, then cathodoluminescent light emitted from the specimen 4 by illumination of the electron beam on the specimen can be detected by the cathodoluminescence detector within the objective lens 13.

It is to be understood that the present invention is not limited to the embodiments described above. For example, the present invention can be applied to any scanning electron microscope as long as the magnetic field of the objective lens reaches the specimen.

Furthermore, in the scanning electron microscope in accordance with the present invention, the secondary electron detector may be installed above the objective lens.

In addition, the scanning electron microscope in accordance with the present invention may be equipped with all of a secondary electron detector, a backscattered electron detector, an X-ray detector, and a cathodoluminescence detector. The microscopist may select the detector according to the purpose.

In the scanning electron microscope in accordance with the present invention, the polepieces of the objective lens are provided with bores to permit various detectors such as backscattered electron detector, X-ray detector, and cathodoluminescence detector to be withdrawably brought to the optical axis. As a result, backscattered electrons, X-rays, and cathodoluminescent light can be efficiently detected at a short working distance and at the same specimen position. The short working distance is necessary for high-resolution detection of secondary electrons. Accordingly, high-resolution secondary electron images and high-brightness backscattered electron images can be obtained from the same field of view. Also, high-sensitivity X-ray analysis is possible.

Having thus described my invention with the detail and particularity required by the Patent Laws, what is desired protected by Letters Patent is set forth in the following claims.

What is claimed is:

1. A scanning electron microscope comprising:
   an electron gun for emitting an electron beam along an electron beam optical axis;
   a system of condenser lenses for focusing the electron beam emitted from said electron gun;
   a scanning means for scanning a specimen with the electron beam emitted from said electron gun;
   an objective lens having inner and outer magnetic polepieces to form a magnetic field lens below the lower ends of the magnetic polepieces;
   a backscattered electron detector for detecting electrons backscattered out of said specimen; and
   an electron beam path formed inside said objective lens, said inner and outer magnetic polepieces provided with opposed bores transverse to the optical axis via at least one of which bores said backscattered electron detector can be withdrawably inserted into said electron beam path inside the objective lens.

2. A scanning electron microscope comprising:
   an electron gun for emitting an electron beam along an electron beam optical axis;
   a system of condenser lenses for focusing the electron beam emitted from said electron gun;
   a scanning means for scanning a specimen with the electron beam emitted from said electron gun;
   an objective lens having inner and outer magnetic polepieces to form a magnetic field lens below the lower ends of the magnetic polepieces;
   an X-ray detector for detecting X-rays emitted from said specimen; and
   an electron beam path formed inside said objective lens;
   said inner and outer magnetic polepieces provided with opposed bores transverse to the optical axis via at least one of which bores said X-ray detector can be withdrawably inserted into said electron beam path within the objective lens.

3. A scanning electron microscope comprising:
   an electron gun for emitting an electron beam along an electron beam optical axis;
   a system of condenser lenses for focusing the electron beam emitted from said electron gun;
   a scanning means for scanning a specimen with the electron beam emitted from said electron gun;
   an objective lens having inner and outer magnetic polepieces to form a magnetic field lens below the lower ends of the magnetic polepieces;
   a cathodoluminescence detector for detecting cathodoluminescent light emitted from said specimen; and
   an electron beam path formed inside said objective lens,
   said inner and outer magnetic polepieces provided with opposed bores transverse to the optical axis via at least one of which bores said cathodoluminescence detector can be withdrawably inserted into said electron beam path inside the objective lens.

4. A scanning electron microscope comprising:
   an electron gun for emitting an electron beam;
   a system of condenser lenses for focusing the electron beam emitted from said electron gun;
   a scanning means for scanning a specimen with the electron beam emitted from said electron gun;
   an objective lens having inner and outer magnetic polepieces to form a magnetic field lens below the lower ends of the magnetic polepieces; and
   an electron beam path formed inside said objective lens;
   wherein said inner and outer polepieces of said objective lens are provided with bores, three in total, via which a backscattered electron detector, an X-ray detector, and a cathodoluminescence detector can be withdrawably inserted into said electron beam path inside the objective lens.

5. The scanning electron microscope of any one of claims 1 to 3, wherein said inner and outer magnetic polepieces are provided with first bores facing said electron beam path and with second bores facing away from said electron beam path, and wherein a secondary electron detector is placed in said second bores.

6. The scanning electron microscope of claim 4, wherein said inner and outer magnetic polepieces have third bores, and wherein a secondary electron detector is placed in said third bores.

7. The scanning electron microscope of any one of claims 1 to 4, wherein a secondary electron detector is placed above said objective lens.

8. The scanning electron microscope of claim 1, wherein said backscattered electron detector is centrally provided with an electron beam passage bore and mounted to a doughnut-like plate.

9. The scanning electron microscope of claim 2, wherein said X-ray detector is centrally provided with an electron beam passage bore and mounted to a doughnut-like plate.

10. The scanning electron microscope of claim 3, wherein said cathodoluminescence detector is centrally provided with an electron beam passage bore and mounted to a doughnut-like plate.

* * * * *